United States Patent [19]

Muirhead, Jr. et al.

[11] Patent Number: 4,513,532
[45] Date of Patent: Apr. 30, 1985

[54] GENETIC FACTOR CAPABLE OF ALTERING LEAF NUMBER AND DISTRIBUTION IN MAIZE

[75] Inventors: Robert C. Muirhead, Jr., Plato Center, Ill.; Donald L. Shaver, Salinas, Calif.

[73] Assignee: Cornnuts Hybrids, Inc., Oakland, Calif.

[21] Appl. No.: 484,791

[22] Filed: Apr. 14, 1983

[51] Int. Cl.³ .............................................. A01G 1/00
[52] U.S. Cl. .................... 47/58; 47/DIG. 1
[58] Field of Search ............................ 47/58, DIG. 1

[56] References Cited

U.S. PATENT DOCUMENTS

| | | | |
|---|---|---|---|
| 3,710,511 | 1/1973 | Patterson | 47/58 |
| 4,051,629 | 10/1977 | Galinat | 47/58 |
| 4,368,592 | 1/1983 | Welch | |

*Primary Examiner*—Robert E. Bagwill
*Attorney, Agent, or Firm*—Townsend & Townsend

[57] ABSTRACT

A single substantially dominant genetic factor which confers an extra leaf phenotype in corn plants provides for the enhanced production of corn in such plants.

Seed corn bearing the genetic factor Lfy (Inbred 101Lfy/Lfy) was deposited at the National Seed Storage Laboratory, Fort Collins, Colo. in March, 1983, and granted laboratory serial no. 174,429 ZM 10235.

27 Claims, No Drawings

GENETIC FACTOR CAPABLE OF ALTERING LEAF NUMBER AND DISTRIBUTION IN MAIZE

BACKGROUND OF THE INVENTION

1. Field of the Invention

The present invention relates generally to the breeding of corn plants and, more particularly, to the manipulation of a genetic factor which alters leaf number and distribution to produce hybrid corn plants having enhanced yields.

Corn (*Zea mays* or maize) is the most extensively grown of all grain crops in the United States. Corn is a naturally cross-pollinated plant where pollen, derived from the male tassel at the top of the plant, is carried by the wind to the female silks produced on the ears of nearby plants. Such natural cross-pollination provides a continuing source of variation in genetic constitution.

It is of great agricultural and economic interest to provide new corn inbreds and hybrids which display an improvement in particular characteristics, such as disease resistance, standability, tolerance to environmental factors, and the like. Through proper breeding techniques, these characteristics can be introduced into new or existing inbred lines of maize which can then be used to produce superior hybrid corn. Hybrid corn is the predominant commercial type.

Heretofore, maize breeders have neglected the intentional manipulation of leaf number and distribution on maize plants. Although breeders have attempted to lower ear placement on maize plants to improve plant standability, the result has generally been a lowering of the physical placement of the ear rather than a change in the proportion of nodes and leaves above and below the ear.

2. Description of the Prior Art

A number of patents relate to the application of genetic principles to the improvement of corn plants. See, for example, U.S. Pat. Nos. 2,753,663; 3,594,152; and 3,710,511; each of which concern the manipulation of genetic male sterility in the production of hybrid maize. See also, U.S. Pat. No. 4,051,629 which relates to the introduction of an alien chromosome to mask the expression of undesirable recessive traits in the production of hybrid seed corn. U.S. Pat. No. 4,351,130 relates to the introduction of a recessive gene for tallness in plants, such as rice, which facilitates the production of hybrid seed. Dugan and Woodworth (1939) J.Am.Soc.Agron. 31:872–875 describe the effect of the removal of leaves from a corn plant on yield.

SUMMARY OF THE INVENTION

The present invention provides for the production of maize having an extra leaf phenotype characterized by an increase in the total number of leaves on each plant, and particularly in an increase in the number of leaves above the ear placement node (EPN), when compared to plants having a normal pheno-type (wild-type). It has been found that such corn plants provide an enhanced yield of corn when compared to normal corn plants having otherwise similar genetic constitutions.

The present invention relies on the identification of corn plants which possess genetic factors capable of conferring the extra leafy phenotype on their progeny. In particular, the present invention relies on a single dominant genetic factor (gene) which was discovered in a mutant hybrid corn plant and which can increase the total leaf number as well as alter the leaf distribution on both inbred and heterotic corn plants. The genetic factor is expressed in all common types of maize and can be maintained in a wide variety of homozygous inbred strains. Such inbred strains which display other desirable characteristics can be crossed using conventional corn breeding techniques to produce hybrid seed corn suitable for commercial corn production.

DESCRIPTION OF THE SPECIFIC EMBODIMENTS

Improved corn plants characterized by genetic factor(s) which confer an extra leaf phenotype are provided. One such genetic factor designated (Lfy) has been derived from a mutant corn plant discovered growing in a field of single cross hybrid corn, as described in detail in the Experimental section below. The Lfy genetic factor acts substantially as a single dominant gene and can be transmitted between strains of corn by conventional breeding techniques. Resulting inbred and hybrid strains display certain favorable characteristics, most notably an increase in yielding ability, disease resistance, and an improved ability to produce photosynthate. Incorporation of the Lfy into an existing strain of corn can improve the yield by up to about thirty percent when compared to the yield of the normal (lfy) counterpart strain.

Such increase in yield results from a number of factors. The increase in total leaf area per acre for a given population of corn plants has a positive effect on yield. While the same result could be achieved by planting a normal (lfy) hybrid at a higher density, the net result would be less efficient in that soil nutrients, sunlight and water would be utilized to support non-productive portions of the additional corn plants. The extra leaf phenotype also provides leaf initiation over an extended period, thus furnishing younger, more vigorous leaves to enhance photosynthesis later in the growth cycle, especially during the grain filling period. Finally, the deeper leaf canopy on the Lfy corn plant supplies protection to the corn silks during very hot weather as well as protecting the plants from other hazards such as hail, insects, disease, and birds.

The method of the present invention is not limited to the particular Lfy factor which has been isolated. Instead, different strains may possess other genetic factors, or combinations of genetic factors, which when crossed with normal strains of corn will produce hybrids having the extra leaf phenotype, as defined below. Use of the Lfy gene, however, is preferred since it has been found to be dominant and stably transmitted to progeny over a number of generations. Moreover, the Lfy gene can easily be incorporated into proven maize inbreds and hybrids which possess other desirable characteristics.

The methods of the present invention can be used to modify and improve growth characteristics of all subspecies of corn, specifically including the dent corns, the flint corns, the soft or flower corns, the sweet corns, the pod corns and the pop corns.

A corn plant having the extra leaf phenotype is characterized by its ability to transmit the phenotype to progeny when crossed with a normal (lfy) plant. The progeny of such a cross will display certain well-defined changes in morphology and growth cycle when compared to the normal parent. First, an increase in total leaf number over the normal parent line is observed. Depending on the maturity of the lfy parent and other factors, the average increase in leaf number will be at least two, generally being from about three to fifteen, usually from about four to ten. The increase is most evident above the ear placement node (EPN) where the average increase will be at least one, generally ranging from about one to ten, usually from about three to six. In addition to the effect on leaf number and distribution, the incorporation of Lfy also increases the number of days required to reach first silk and pollen (anthesis). The increased time to first silk will be at least one day and will generally range from about three to ten days, usually being from about four to eight days. The increased time to anthesis will be at least two days, generally ranging from about five to twenty days, usually about ten to eighteen days. Finally, Lfy often results in higher ear placement in both inbreds and hybrids having the Lfy genetic factor.

In order to determine if a variety possesses the Lfy genetic factor, a classic genetic test for allelism can be performed. For convenience, the variety tested should be homozygous. If necessary, the variety can be made homozygous by conventional techniques, usually backcrossing followed by self pollinization. The homozygous variety is then crossed with a known Lfy/Lfy strain (such as 101Lfy/Lfy, described hereinafter). Then, by self pollinization of the resulting $F_1$ hybrid and observing the progeny, the genotype of the unknown variety can be determined. Specifically, if all progeny display the Lfy phenotype the unknown variety possessed the Lfy gene.

Since the simple addition of Lfy extends plant maturity it is often desirable to incorporate off-setting earliness genetic factor(s). For example, partially dominant major genes for earliness can be transferred from common Gaspe Flint varieties by conventional backcrossing. Other genes which provide for earliness in inbred or hybrid corn are well-known in the art and suitable for the present invention. For a general discussion of earliness conversion, see Shaver (1976) Maize Genetics Cooperation News Letter 50:20–23, the disclosure of which is incorporated herein by reference.

The Lfy genetic factor of the present invention is introduced to new corn lines by crossing two parental strains, at least one of which incorporates the Lfy gene. Any strain of corn which includes at least one Lfy gene can be used as a breeding strain for developing other inbreds and hybrids having the Lfy gene. Conveniently, the transfer of the Lfy gene is accomplished by conventional backcrossing, followed by selfing to render the strains homozygous. For the purposes of enablement, seed corn from the Lfy strain designated 101Lfy/Lfy has been deposited at the National Seed Storage Laboratory of the U.S. Department of Agriculture, Fort Collins, Colo., being granted serial no. 174,429 ZM 10235.

In general, the method of the present invention will be used to produce hybrid corn for commercial corn production. Such hybrid corn is usually a single cross, that is a first generation hybrid between two inbreds. It is desirable that at least one of the two inbred parents be homozygous (Lfy/Lfy) so that the transmission of at least one Lfy gene to all plants of the hybrid is assured. In the more uncommon types of hybrids, such as four-way hybrids, three-way hybrids, and modified single crosses (i.e., "special" or "sisterline" crosses), it will be important that at least one of the parents, however constituted, shall be homozygous for the Lfy gene. In this way, all plants of the resultant commercial hybrid will have at least one Lfy gene and thus uniformly express the extra leaf phenotype. In some situations it will be desirable to produce a final hybrid having individual plants with both normal and Lfy phenotypes in order to spread out silking, pollination, and nutrient usage timing parameters. In such cases, the simplest scheme would be to produce the commercial seed by crossing two parents, one of which is homozygous lfy/lfy, and the other heterozygous Lfy/lfy. Resultant seed corn would yield both Lfy and mormal (lfy) plants as an equal mixture. Other genetic manipulations and/or mixtures of counterparts differing in the Lfy allele could be employed to adjust the resultant mixture in the hybrid seed to any desired proportion of Lfy and lfy plants.

Lfy/Lfy inbreds can also be obtained by inbreeding from populations into which the Lfy gene has previously introduced. By selection and evaluation during inbreeding lines can be obtained which are pure for other desired characteristics. In particular, those inbreds which are homozygous for Lfy and have an assortment of non-allelic genes complementing the Lfy phenotype will be chosen. In addition, other valuable characteristics such as disease resistance, insect resistance, strength of stalk and the like may also be selected.

After a number of Lfy inbreds which display a range of desirable characteristics are developed, experimental hybrids will be produced and those hybrids which excel in many or all attributes identified. After such optimum combinations are determined, the parental inbred lines are increased and large quantities of parental seedstock produced by well-known techniques.

In summary the present invention provides a genetically transmitted characteristic which can be selectively incorporated in hybrid seed corn, together with desirable genetic characteristics, to produce superior hybrid and inbred corn lines. The invention employs well-known corn breeding techniques, such as those described in Corn and Corn Improvement, Sprague ed., American Society of Agronomy, Publication No. 18, Madison, Wis. (1977), the disclosure of which is incorporated herein by reference.

The following experimental results are offered by way of example and not by way of limitation.

EXPERIMENTAL

The inbred designations used herein are based upon the system set forth in Henderson, "Maize Research and Breeders Manual No. IX," Illinois Foundation Seeds, Inc., Champaign, Ill. (1980).

1. Leaf Number Inheritance in Normal Maize

Average leaf number and leaf distribution were determined for twenty-six normal (lfy/lfy) inbred lines of maize. The results are shown in Table 1.

TABLE 1

| Inbred Line | Leaves Below EPN[a] | Leaves Above EPN[a] | Total |
|---|---|---|---|
| F2 | 11.21 ± 0.412 | 3.86 ± 0.480 | 15.07 ± 0.677 |
| F7 | 10.16 ± 0.616 | 3.29 ± 0.496 | 13.45 ± 0.702 |
| Mo17 | 13.17 ± 1.160 | 4.85 ± 0.594 | 18.02 ± 1.145 |
| CI21E | 17.03 ± 0.796 | 5.45 ± 0.624 | 22.48 ± 0.963 |
| Va26 | 13.00 ± 0.455 | 6.37 ± 0.616 | 19.37 ± 1.106 |
| N28 | 17.03 ± 0.843 | 7.25 ± 0.704 | 24.28 ± 1.043 |
| B37 | 13.22 ± 0.570 | 6.46 ± 0.505 | 19.68 ± 0.866 |
| K55W | 16.46 ± 0.857 | 7.25 ± 0.605 | 23.71 ± 0.911 |
| Va60 | 12.49 ± 0.837 | 5.32 ± 0.474 | 17.81 ± 0.938 |
| T × 61M | 16.80 ± 0.894 | 5.65 ± 0.626 | 22.45 ± 1.026 |
| B73 | 16.48 ± 0.624 | 5.68 ± 0.504 | 22.16 ± 0.668 |
| H96 | 13.60 ± 0.675 | 4.60 ± 0.498 | 18.20 ± 0.961 |
| H100 | 15.85 ± 0.662 | 6.64 ± 0.623 | 22.49 ± 0.823 |

TABLE 1-continued

| Inbred Line | Leaves Below EPN[a] | Leaves Above EPN[a] | Total |
|---|---|---|---|
| NC238 | 17.24 ± 0.908 | 8.22 ± 0.599 | 25.46 ± 0.944 |
| 337 | 16.40 ± 1.195 | 8.02 ± 0.821 | 24.42 ± 1.092 |
| 341W | 15.94 ± 0.619 | 8.06 ± 0.586 | 24.00 ± 0.728 |
| T × 602 | 18.76 ± 0.766 | 6.61 ± 1.080 | 25.37 ± 1.142 |
| A632 | 12.47 ± 0.604 | 6.26 ± 0.602 | 18.73 ± 0.724 |
| A632E[b] | 11.19 ± 0.945 | 5.61 ± 0.497 | 16.80 ± 1.077 |
| A634 | 14.24 ± 0.698 | 6.12 ± 0.477 | 20.36 ± 0.884 |
| 637 | 12.61 ± 0.560 | 5.48 ± 0.569 | 18.09 ± 0.597 |
| 637E[b] | 10.83 ± 0.381 | 5.03 ± 0.719 | 15.86 ± 0.731 |
| A619 | 10.79 ± 0.520 | 5.90 ± 0.431 | 16.69 ± 0.681 |
| 914 | 11.63 ± 0.670 | 6.03 ± 0.557 | 17.66 ± 1.029 |
| 914E[b] | 8.52 ± 0.768 | 5.06 ± 0.681 | 13.58 ± 0.810 |
| 957 | 16.53 ± 0.754 | 6.23 ± 0.509 | 22.76 ± 0.818 |

[a]Average of 1066 plants.
[b]The suffix E designates an earliness conversion of the inbred line in which two partially dominant major genes for earliness have been transferred from Gaspe Flint by means of ten uninterrupted backcrosses and made homozygous in two sibbing, then two selfing generations.

These results indicate that average leaf number for normal inbred lines typically ranges from about 13 to 25, while the average number of leaves located above the ear placement node (EPN) typically ranges from 4 to 7. Later maturing inbred lines, such as NC238, tend to have greater leaf numbers, while early lines, like $F_7$, tend to have fewer leaves.

In order to gain information concerning the inheritance of leaf number difference in normal maize, two inbreds of similar physiological maturity, but having widely differing numbers of leaves above the EPN were selected. An $F_1$ was produced, as well as an $F_2$, and backcrosses to each of the two parents. Data are presented in Table 2.

TABLE 2

| | Leaf Number Above EPN | | | | | | | Average |
|---|---|---|---|---|---|---|---|---|
| | 4 | 5 | 6 | 7 | 8 | 9 | 10 | 11 | |
| Missouri 17 | 12 | 29 | 5 | | | | | | 4.85 ± .594 |
| Inbred 337 | | | | 6 | 26 | 11 | | | 8.12 ± .617 |
| 17 × 337 F1 | | | | 17 | 35 | 8 | 2 | | 7.92 ± .736 |
| 17 × 337 F2 | 1 | 1 | 22 | 87 | 89 | 25 | 7 | 1 | 7.59 ± .979 |
| (17 × 337) 17 | | 3 | 60 | 152 | 33 | | | | 6.87 ± .638 |
| (17 × 337) 337 | 1 | 1 | 8 | 76 | 102 | 37 | 2 | | 7.74 ± .850 |

Missouri 17 and inbred 337 differ markedly in leaf number above the EPN, having non-overlapping distributions. Their $F_1$ hybrid has an intermediate leaf number, skewed towards that of the higher parent, presumably because of heterosis. The $F_2$ has a wider distribution of leaf numbers, exceeding that of the higher parent. The two backcross progenies have slightly narrower distributions, in each case skewed towards that of the recurrent parent. The segregation observed in this study is typical of a quantitative trait. See, Goodenough, *Genetics*, Saunders College, Philadelphia (1978) pp. 640–643.

The effect of mass selection for increased leaf number above the EPN was examined in a synthetic population designated 139G and available from Cornnuts Hybrids, Inc., Salinas, Calif. The results, shown in Table 3, are characteristic of a quantitatively inherited trait.

TABLE 3

| | Leaf Number Above EPN | | | | | | | | | Average |
|---|---|---|---|---|---|---|---|---|---|---|
| | 4 | 5 | 6 | 7 | 8 | 9 | 10 | 11 | 12 | |
| Unselected | 8 | 193 | 177 | 39 | 3 | 1 | | | | 5.60 ± .729 |
| Second Cycle | 5 | 144 | 178 | 96 | 55 | 18 | 7 | 1 | | 6.32 ± 1.214 |
| Third Cycle | 3 | 142 | 210 | 237 | 146 | 104 | 45 | 6 | 1 | 7.02 ± 1.421 |

2. Derivation of Extra Leaf Factor (Lfy)

The extra leaf factor (Lfy) of the present invention was derived from a mutant maize plant growing near Plato Center, Ill. in a field of single cross hybrid having the pedigree A632xM16. The discovery plant had four seed-bearing ears and a greater than normal number of leaves. Seed from this plant was selfed over five generations until homozygous. Such homozygous seedcorn (Lfy/Lfy) designated Inbred 101 Lfy/Lfy has been deposited at the National Seed Storage Laboratory, Fort Collins, Colo., and has been granted serial no. 174,429 ZM 10235.

3. Leaf Distribution in Normal and Lfy Inbreds and Crosses Thereof

Three normal and one Lfy inbred were crossed ($F_1$), backcrossed and test crossed, and the effect on leaf distribution observed. The results are set forth in Table 4.

TABLE 4

| | Leaf Number Above EPN | | | | | | | | | | | | | | | Avg |
|---|---|---|---|---|---|---|---|---|---|---|---|---|---|---|---|---|
| | 4 | 5 | 6 | 7 | 8 | 9 | 10 | 11 | 12 | 13 | 14 | 15 | 16 | 17 | 18 | |
| Inb. 101Lfy | | | | | 1 | 5 | 14 | 47 | 57 | 16 | 6 | 2 | | | | |
| Inb. 293 | 1 | 88 | 36 | 5 | | | | | | | | | | | | |
| Inb. 957 | | 2 | 22 | 73 | 12 | | | | | | | | | | | |
| Inb. 914 | | 8 | 83 | 51 | 1 | | | | | | | | | | | |
| 101Lfy × 293 F1 | | | | 2 | 30 | 56 | 92 | 58 | 25 | 10 | 6 | 3 | 1 | | | |
| 101Lfy × 293 F2 | 1 | 13 | 44 | 26 | 5 | 45 | 57 | 52 | 46 | 19 | 11 | 6 | 2 | 1 | | |
| (101Lfy × 293)293 | 1 | 66 | 99 | 29 | 6 | 27 | 55 | 53 | 35 | 19 | 11 | 3 | | 2 | | |
| (101Lfy × 293)101Lfy | | | 3 | 13 | 31 | 60 | 75 | 46 | 31 | 22 | 11 | 4 | | | | |
| (101Lfy293)957 | 1 | 34 | 148 | 86 | 19 | 58 | 91 | 70 | 36 | 17 | 9 | 4 | | | | |
| 957 × (101Lfy × 293) | | 44 | 172 | 80 | 12 | 53 | 89 | 75 | 38 | 22 | 11 | 6 | 5 | 2 | 1 | |
| 914 × (101Lfy × 293) | | 6 | 33 | 30 | 2 | 13 | 28 | 19 | 7 | 2 | 1 | | | | | |

These results indicate that Lfy is a single dominant genetic factor (gene) capable, when crossed with normal inbreds, of producing hybrid corn displaying greatly enhanced leaf number, especially above the EPN. Statistical analysis confirms the single dominant gene model with a probability of 0.90.

4. Conversion of Normal Inbred Lines to Leafy

Six normal inbred lines were converted to Lfy/Lfy by conventional backcrossing from 101 Lfy/Lfy. The converted lines were selfed until homozygous, and the effect on total leaf number and leaf distribution was observed. The results are set forth in Table 5.

TABLE 5

| Inbred | Leaves Below EPN | Leaves Above EPN | Total Leaves |
|---|---|---|---|
| A632 | 12.47 ± 0.604 | 6.25 ± 0.602 | 18.73 ± 0.724 |
| A632 Lfy/Lfy | 16.06 ± 0.998 | 10.23 ± 0.845 | 26.29 ± 1.270 |
| A632E[a] | 11.19 ± 0.945 | 5.61 ± 0.497 | 16.80 ± 1.077 |
| A632E[a] Lfy/Lfy | 12.10 ± 0.831 | 9.32 ± 0.792 | 21.42 ± 0.985 |
| 637 | 12.61 ± 0.560 | 5.48 ± 0.569 | 18.09 ± 0.597 |
| 637 Lfy/Lfy | 14.00 ± 0.632 | 9.77 ± 1.006 | 23.77 ± 0.920 |
| 637E[a] | 10.83 ± 0.381 | 5.03 ± 0.719 | 15.86 ± 0.731 |
| 637E[a] Lfy/Lfy | 12.73 ± 0.451 | 9.73 ± 0.981 | 22.46 ± 1.042 |
| 914 | 11.63 ± 0.670 | 6.03 ± 0.557 | 17.66 ± 1.029 |
| 914 Lfy/Lfy | 12.97 ± 0.606 | 9.10 ± 0.651 | 22.07 ± 0.931 |
| 957 | 16.53 ± 0.754 | 6.23 ± 0.509 | 22.76 ± 0.818 |
| 957 Lfy/Lfy | 16.07 ± 0.584 | 9.43 ± 0.729 | 25.50 ± 0.974 |

[a]See Table 1 for explanation.

These results demonstrate that the incorporation of the Lfy genetic factor significantly increases the total leaf number, particularly increasing the number of leaves above the EPN.

5. Comparison of Leafy Genetic Factor With Other Quantitative Genes for High Leaf Number A high leaf number normal inbred 337 was crossed with a converted leafy inbred W64a Lfy/Lfy. The backcross was produced, and the leaf count for each of the inbreds and hybrids is set forth in Table 6.

The distribution frequencies of plants having specified leaf numbers above EPN are given in Table 7.

The data in Table 7 show enhanced leaf number in the F₁ compared to either inbred parent, indicating that Lfy factor acts together with other factors contributed by 337. The magnitude of the increase indicates that the Lfy factor for higher leaf number is not allelic to those contributed by 337. The evident bimodality of the backcross is added evidence that Lfy acts as a single dominant gene. These data confirm that normal inbreds having high leaf numbers do not already possess the Lfy gene and, as indicated by the data in Table 2, derive their higher leaf numbers from the action of quantitative genes.

6. Stability of the Leafy Gene

Referring to the data of Table 4, a comparison of the frequency of transmission of Lfy from heterozygotes reveals no significant statistical difference between male and female transmission. This result demonstrates that the Lfy gene is almost certainly a stable point mutation and that it does not result from inherently unstable duplication or deficiency of chromosomal segments.

Stability was further confirmed by demonstrating that leaf number variation among plants having identical genotype is due to random variation rather than a differing state of the Lfy allele.

TABLE 6

| | Leaves Below Ear | Leaves Above EPN | Total |
|---|---|---|---|
| 337 | 15.70 ± 0.707 | 8.12 ± 0.617 | 23.82 ± 0.886 |
| W64aLfy/Lfy | 14.49 ± 0.581 | 9.49 ± 1.445 | 23.98 ± 1.521 |
| 337 × W64aLfy | 14.13 ± 0.509 | 14.43 ± 1.431 | 28.56 ± 1.612 |
| (337 × W64aLfy) × 337 | 14.27 ± 1.225 | 9.74 ± 2.722 | 24.01 ± 3.143 |

TABLE 7

| | 5 | 6 | 7 | 8 | 9 | 10 | 11 | 12 |
|---|---|---|---|---|---|---|---|---|
| Inb. 337 | | | 6 | 26 | 11 | | | |
| W64aLfy/Lfy | | | | 1 | 13 | 12 | 15 | 2 |
| F₁ Hybrid | | | | | | | | |
| Backcross | 1 | 13 | 48 | 47 | 21 | 20 | 21 | 25 |

| | 13 | 14 | 15 | 16 | 17 | 18 | Average |
|---|---|---|---|---|---|---|---|
| Inb. 337 | | | | | | | 8.12 |
| W64aLfy/Lfy | 1 | 1 | | | | | 9.49 |
| F₁ Hybrid | 9 | 9 | 7 | 2 | 1 | 2 | 14.43 |
| Backcross | 14 | 7 | 11 | 4 | 2 | 1 | 9.94 |

TABLE 8

| | 4 | 5 | 6 | 7 | 8 | 9 | 10 | 11 | 12 | 13 | 14 | 15 | 16 |
|---|---|---|---|---|---|---|---|---|---|---|---|---|---|
| Male Side[a] | | | | | | | | | | | | | |
| Low[b] | | 19 | 74 | 41 | 5 | 27 | 44 | 32 | 19 | 11 | 3 | | 2 |
| High[c] | | 22 | 78 | 32 | 6 | 23 | 37 | 35 | 17 | 11 | 5 | 5 | 1 |
| Female Side | | | | | | | | | | | | | |
| Low[b] | | 14 | 57 | 29 | 8 | 20 | 32 | 23 | 16 | 5 | 1 | | |
| High[c] | 1 | 7 | 26 | 19 | 3 | 12 | 17 | 13 | 4 | 7 | 4 | | |

[a]Lfy/lfy single cross
[b]Testcross from plants in the hybrid 101 Lfy/Lfy × 293 having unusually low leaf number above the EPN.
[c]Testcross from plants in the hybrid 101 Lfy/Lfy × 293 having unusually high leaf number above the EPN.

A large population of the F₁ hybrid 101Lfyx293 (see Table 4) was grown out, and test crosses made from plants having unusually high or unusually low numbers of leaves above the EPN. The results are set forth in Table 8.

The data in Table 8 reveal no statistical difference between leaf number in progeny derived from parental plants with either high or low leaf number, or in rate of transmission of Lfy on the male or female side of the testcross. The stability of Lfy is thus further supported.

7. The Effect of Lfy on Flowering Time and Ear Placement

The apical meristem of the maize plant cuts off all of the above ground parts of the plant sucessively before forming the tassel. It would therefore be expected that Lfy plants should reach anthesis (pollen shed) later than normal plants because a larger number of leaves have to be produced before tassel differentiation. An experiment was conducted to quantitate the difference in reaching anthesis between isogenic Lfy and normal plants. The results are shown in Table 9.

TABLE 9

| Number of Leaves Above EPN | Number of Plants | Mean Number of Days to Anthesis |
|---|---|---|
| 5 | 5 | 80.00 ± 3.54 |
| 6 | 3 | 79.04 ± 2.59 |
| 7 | 56 | 78.18 ± 2.68 |
| 8 | 9 | 80.50 ± 3.39 |
| 9 | 18 | 85.22 ± 2.21 |
| 10 | 38 | 87.50 ± 3.44 |
| 11 | 37 | 89.73 ± 3.18 |
| 12 | 21 | 90.48 ± 3.08 |
| 13 | 2 | 91.00 ± 1.41 |
| 14 | 2 | 95.00 ± 2.83 |
| 15 | | 93.00 |

The data show that plants which have more leaves are later to reach anthesis. Also, the clear bimodality of these data is further confirmation of the single gene model for inheritance of extra leaves.

Data presented below in Table 10 compare the days to silk, days to anthesis, and the number of leaves above the EPN in Lfy and normal counterparts of the hybrid Hy$^2$ExA632.

The data in Table 10 show that higher ear placement is favored in Lfy inbreds and hybrids, and that the EPN is intermediate between those of the two parents. In total leaves per plant, the normal hybrid was intermediate, while the Lfy hybrid had the same leaf number as the Lfy inbred parent. There was a delay in anthesis in the Lfy hybrid of about 14 days, but the delay to first silking was only 4.5 days. The rather large standard deviation in days to anthesis in the Lfy hybrid indicates a considerable spread in individual plants, but this works to avoid lack of pollen for the first silks to emerge in a normal Lfy hybrid. However, by manipulation of E factors or by shifting earlier inbreds into hybrid pedigrees, the delay in maturity can be offset. Insertion of E factors also tends to offset the tendency for higher ear placement, and hybrids having the combination of Lfy and E produce ears from essentially the same node (Table 5).

8. Effect of Lfy on Leaf Area Per Plant

Leaf measurement data were taken from the two hybrids shown in Table 10. Normal and leafy counterparts of ten randomly chosen plants were examined. Odd numbered leaves were actually measured, and the leaf parameters from the interspersed even numbered leaves were estimated as the average of the leaf immediately above and the leaf immediately below. The results are set for in Table 11.

The data in Table 11 were used to estimate the total leaf area above EPN in both the normal and Lfy counterparts of Hy$^2$xA632. The leaf area in the normal line was estimated to be 408.47 in$^2$, and in the Lfy hybrid to be 600.94 in$^2$. Since ear placement is 1.05 nodes higher in the Lfy counterpart, one can multiply this number by the area of the thirteenth leaf at approximately the EPN to estimate that the Lfy version has 92 square inches more leaf area below the ear than the normal counterpart. The total extra leaf area per plant due to the Lfy factor is thus estimated to be 284.2 in$^2$ (600.94−408.92+92).

9. Degree of Dominance of the Lfy Gene.

An experiment was conducted to assess the degree of phenotypic dominance for Lfy by comparing homozygous Lfy/Lfy hybrids with their heterozygous Lfy/lfy counterparts. Results are shown in Table 12.

It is evident that homozygous Lfy/Lfy hybrids have a significantly (P=0.002) greater number of leaves below the ear, by an average of 0.96 leaves. However, homozygous Lfy/Lfy hybrids also have slightly lower number of leaves above the ear (although this difference is non-significant at the 5% level). Based on these observations, Lfy may not be completely phenotypically dominant.

10. Yield Comparison between a Normal Hybrid and its Leafy Conversion

A yield comparison was run between test cross hybrids of normal and Lfy counterparts of the same strain. Lfy/lfy segregants (obtained from backcrossing A632 Lfy into A632) were test crossed into the sister cross hybrid 774x747, and ear samples were grown out. Remnant seed from the testcrosses which were determined to be uniformly Lfy/lfy were then composited and used to test against a composite of those determined to be uniformly lfy/lfy.

TABLE 10

|  | Number Plants | EPN | Total Leaves Per Plant | Days to Anthesis | Days to First Silk |
|---|---|---|---|---|---|
| Inb. Hy$^2$E$^a$ | 24 | 12.17 ± .379 | 16.83 ± .480 |  |  |
| Inb. A632 | 22 | 15.50 ± 1.012 | 21.91 ± .867 |  |  |
| Inb. A632Lfy/Lfy | 79 | 16.66 ± 1.449 | 26.04 ± 2.165 |  |  |
| Hy$^2$E × A632 | 22 | 13.68 ± .488 | 19.36 ± .848 | 72.36 ± 1.605 | 71.95 ± 1.96 |
| Hy$^2$ × A632Lfy/Lfy | 22 | 14.73 ± .828 | 26.36 ± 1.560 | 86.91 ± 3.558 | 76.55 ± 2.35 |

$^a$See Table 1 for explanation.

TABLE 11

| Leaf Number | Number Of Plants | Hy$^2$E × A632Lfy/lfy | | | Number Of Plants | Hy$^2$E × A632 | | |
|---|---|---|---|---|---|---|---|---|
| | | Length | Width | Area$^a$ | | Length | Width | Area$^a$ |
| 11 | 10 | 32.15 | 2.99 | 72.10 | 10 | 31.86 | 2.94 | 70.37 |
| 12 |  |  |  | 79.80 |  |  |  | 77.64 |
| 13 | 10 | 33.39 | 3.50 | 87.65 | 10 | 32.16 | 3.52 | 84.90 |
| 14 |  |  |  | 85.64 |  |  |  | 81.16 |
| 15 | 10 | 31.32 | 3.56 | 83.62 | 10 | 27.24 | 3.79 | 77.43 |
| 16 |  |  |  | 76.28 |  |  |  | 69.88 |
| 17 | 10 | 27.69 | 3.32 | 68.95 | 10 | 24.09 | 3.45 | 62.33 |
| 18 |  |  |  | 62.54 |  |  |  | 47.90 |
| 19 | 10 | 24.30 | 3.08 | 56.13 | 10 | 17.29 | 2.58 | 33.46 |
| 20 |  |  |  | 50.94 |  |  |  | 24.89 |
| 21 | 10 | 21.86 | 2.79 | 45.74 | 1 | 12,80 | 1.70 | 16.32 |
| 22 |  |  |  | 40.40 |  |  |  |  |
| 23 | 10 | 18.41 | 2.54 | 35.07 |  |  |  |  |
| 24 |  |  |  | 28.83 |  |  |  |  |
| 25 | 8 | 15.29 | 1.97 | 22.59 |  |  |  |  |
| 26 |  |  |  | 18.66 |  |  |  |  |
| 27 | 4 | 11.70 | 1.68 | 14.74 |  |  |  |  |
|  | (EPN = 14.73) | | | | (EPN = 13.68) | | | |

$^a$Areas of even numbered leaves were interpolated as intermediate values between those of the odd numbered leaves as actually measured. Area was calculated as length × width × 0.75.

TABLE 12

| Hybrid | Constitution for Lfy | Leaves Below EPN | Leaves Above EPN | Total Leaves |
|---|---|---|---|---|
| 632E × 637E | Heterozygous | 12.28 ± 0.944 | 12.44 ± 1.537 | 24.72 ± 2.212 |
|  | Homozygous | 12.67 ± 0.967 | 11.06 ± 1.308 | 23.73 ± 1.723 |
| 632E × 637 | Heterozygous | 12.94 ± 1.120 | 10.56 ± 1.423 | 23.50 ± 2.035 |
|  | Homozygous | 13.64 ± 1.791 | 10.08 ± 1.401 | 23.72 ± 2.173 |
| 632E × 957 | Heterozygous | 13.31 ± 1.283 | 10.67 ± 1.707 | 23.98 ± 2.580 |
|  | Homozygous | 14.36 ± 1.046 | 12.67 ± 1.639 | 27.03 ± 2.077 |
| 632 × 637E | Heterozygous | 13.17 ± 0.845 | 11.83 ± 1.577 | 25.00 ± 1.707 |
|  | Homozygous | 14.83 ± 0.910 | 11.14 ± 0.990 | 25.97 ± 1.231 |
| 632 × 637 | Heterozygous | 14.25 ± 0.840 | 10.14 ± 1.693 | 24.39 ± 2.142 |
|  | Homozygous | 15.50 ± 0.845 | 10.08 ± 1.105 | 25.58 ± 1.645 |
| 632 × 957 | Heterozygous | 15.17 ± 1.108 | 12.69 ± 2.847 | 27.86 ± 2.332 |
|  | Homozygous | 16.39 ± 1.023 | 12.17 ± 1.521 | 28.56 ± 1.229 |
| 637E × 957 | Heterozygous | 13.00 ± 1.069 | 12.61 ± 2.781 | 25.61 ± 2.441 |
|  | Homozygous | 14.06 ± 0.583 | 10.28 ± 0.701 | 24.34 ± 1.642 |
| 637 × 957 | Heterozygous | 14.97 ± 0.971 | 8.94 ± 0.630 | 23.91 ± 0.967 |
|  | Homozygous | 15.69 ± 0.709 | 8.61 ± 0.804 | 24.30 ± 1.036 |
| 914 × 957 | Heterozygous | 14.37 ± 0.872 | 9.17 ± 0.845 | 23.56 ± 1.158 |
|  | Homozygous | 15.00 ± 0.894 | 9.22 ± 0.989 | 24.22 ± 1.098 |
|  | Average for Heterozygous | 13.72 | 11.01 | 24.73 |
|  | Average for Homozygous | 14.68 | 10.59 | 25.27 |

The comparison was thus between testcross hybrids of normal and Lfy full sibs. The results are set forth in Table 13.

TABLE 13

| Hybrid | Yield[a] | Ear Lodged | Ear Height | Ears Per Plant | Percent Full Stand | Field Moisture |
|---|---|---|---|---|---|---|
| Normal | 3,875 | 0.0 | 46.9 | .959 | 100.7 | 25.6 |
| Leafy | 5,012 | 0.0 | 52.1 | .914 | 97.2 | 26.8 |

[a]Pounds of corn per acre, 15.5% moisture.

Hybrid means values were compared by the "t" statistic method, giving a value of 3.56, and a probability of less than 0.001. These data indicate a yield advantage of about 29%.

Although the foregoing invention has been described in some detail by way of illustration and example for purposes of clarity and understanding, it will be obvious that certain changes and modifications may be practiced within the scope of the appended claims.

What is claimed is:

1. A method for producing hybrid seed corn, said method comprising crossing first and second maize plants, where at least one of said maize plants is characterized by a genetic factor which confers an extra leaf phenotype, said genetic factor being capable of transmission to said hybrid seed corn substantially as a single dominant gene.

2. Hybrid seed corn produced as in claim 1.

3. A method for producing seed corn, said method comprising:
   pollinating a maize plant with pollen, wherein at least one of the maize plant and the pollen possess a single, substantially dominant genetic factor which confers an extra leaf phenotype on the maize grown from the seed corn; and
   harvesting seed produced on the pollinated maize plant.

4. A method as in claim 3, wherein the pollen is derived from the maize plant which is pollinated.

5. A method as in claim 3, wherein the pollen is derived from other than the maize plant which is pollinated.

6. Seed corn produced by the method of claim 3.

7. A corn plant grown from the seed corn of claim 6.

8. A hybrid maize plant characterized by a genetic factor which confers an extra leaf phenotype, said genetic factor being capable of transmission to progeny substantially as a single dominant gene.

9. Seed corn derived from the hybrid maize plant of claim 8.

10. Seed corn as in claim 9, wherein the maize plant was the male parent.

11. Seed corn as in claim 9, wherein the maize plant was the female parent.

12. Hybrid seed corn characterized by a single, substantially dominant genetic factor which confers an extra leaf phenotype on the maize grown from the seed corn.

13. Seed corn as in claim 12, which seed corn is homozygous for said genetic factor.

14. Seed corn as in claim 12, which seed corn is heterozygous for said genetic factor.

15. A hybrid corn plant capable of conferring an extra leaf phenotype on its progeny when crossed with a corn plant which does not display said extra leaf phenotype, said extra leaf phenotype characterized by (1) an increase in average total leaf number of at least two, (2) an increase in average leaf number above the ear placement node of at least one, (3) an increase in average number of days to first silk of at least one, and (4) an increase in average number of days to anthesis of at least five.

16. Seed corn derived from the plant of claim 15.

17. A hybrid corn plant which is homozygous or heterozygous in the Lfy genetic factor which is possessed by the strain designated Inbred 101Lfy/Lfy having serial number 174,429 ZM 10235 of the National Seed Storage Laboratory, Fort Collins, Colo.

18. A method for producing hybrid seed corn, said method comprising crossing first and second corn plants, where at least one of said corn plants is characterized by the Lfy genetic factor which is possessed by the strain designated Inbred 101Lfy/Lfy having serial number 174,429 ZM 10235 of the National Seed Storage Laboratory, Fort Collins, Colo.

19. Seed corn produced by the method of claim 18.

20. A genetic factor derived from corn, which genetic factor is capable of conferring an extra leaf phenotype which is capable of transmission to progeny substantially as a single dominant gene.

21. A genetic factor derived from corn, which genetic factor is capable of conferring an extra leaf phenotype when introduced to a corn plant which would otherwise not display said extra leaf phenotype, said extra leaf phenotype characterized by (1) an increase in average leaf number of at least two, (2) an increase in average leaf number above the ear placement node of at least one, (3) an increase in average number of days to first silk of at least one, and (4) an increase in average number of days to anthesis of at least five.

22. A Lfy genetic factor which is derived from the corn strain designated 101Lfy/Lfy having serial number 174,429 ZM 10235 of the National Seed Storage Laboratory, Fort Collins, Colo.

23. A method for producing inbred seed corn characterized by a genetic factor capable of conferring an extra leaf phenotype which is capable of transmission to progeny substantially as a single dominant gene, said method comprising inbreeding a corn plant which is characterized by said genetic factor until the genetic composition of the progeny of such inbreeding becomes substantially constant.

24. Seed corn produced by the method of claim 23.

25. A corn plant grown from the seed corn of claim 24.

26. A homozygous genetic factor maintained by self-pollinating a corn plant possessing said factor through at least one generation until said factor is homozygous, said genetic factor being capable of conferring an extra leaf phenotype which is transmittable to progeny substantially as a single dominant gene.

27. A homozygous genetic factor maintained by backcrossing a first corn plant with a second corn plant possessing said factor, said genetic factor being capable of conferring an extra leaf phenotype which is transmittable to progeny substantially as a single dominant gene.

* * * * *

UNITED STATES PATENT AND TRADEMARK OFFICE
CERTIFICATE OF CORRECTION

PATENT NO. : 4,513,532

DATED : April 30, 1985

INVENTOR(S) : Robert C. Muirhead, Jr., and Donald L. Shaver

It is certified that error appears in the above-identified patent and that said Letters Patent is hereby corrected as shown below:

On the title page;

Change the Assignee from Cornnuts Hybrids, Inc., Oakland, Calif. to Lfy Partners Limited, Oakland, Calif.

Signed and Sealed this

Twenty-fourth Day of September 1985

[SEAL]

Attest:

DONALD J. QUIGG

Attesting Officer

Commissioner of Patents and Trademarks—Designate